United States Patent
Hunsicker et al.

(10) Patent No.: US 9,358,356 B2
(45) Date of Patent: Jun. 7, 2016

(54) COMPENSATION FOR UNMEASURABLE INSPIRATORY FLOW IN A CRITICAL CARE VENTILATOR

(71) Applicant: General Electric Company, Schenectady, NY (US)

(72) Inventors: Paul Hunsicker, Hales Corners, WI (US); Matthew Michael Stephenson, Cottage Grove, WI (US); Jessica B. Payne, Madison, WI (US)

(73) Assignee: General Electric Company, Schenectady, NY (US)

( * ) Notice: Subject to any disclaimer, the term of this patent is extended or adjusted under 35 U.S.C. 154(b) by 92 days.

(21) Appl. No.: 14/023,975

(22) Filed: Sep. 11, 2013

(65) Prior Publication Data

US 2014/0014093 A1  Jan. 16, 2014

Related U.S. Application Data

(62) Division of application No. 12/695,514, filed on Jan. 28, 2010, now abandoned.

(51) Int. Cl.
*A61M 16/00* (2006.01)
*A61M 11/00* (2006.01)
*A61M 16/12* (2006.01)
(Continued)

(52) U.S. Cl.
CPC ............ *A61M 16/0051* (2013.01); *A61M 11/00* (2013.01); *A61M 16/0057* (2013.01); *A61M 16/12* (2013.01); *A61M 16/14* (2013.01); *A61M 16/202* (2014.02); *A61M 2016/0039* (2013.01); *A61M 2016/0042* (2013.01)

(58) Field of Classification Search
CPC ............ A61M 16/00; A61M 16/0051; A61M 16/0003; A61M 16/0015; A61M 16/0018; A61M 16/0024; A61M 16/0027; A61M 16/003; A61M 16/0033; A61M 16/0036; A61M 16/0039; A61M 16/0042; A61M 16/10; A61M 16/12; A61M 16/14

See application file for complete search history.

(56) References Cited

U.S. PATENT DOCUMENTS

| 4,340,044 A | 7/1982 | Levy et al. |
| 5,237,987 A | 8/1993 | Anderson et al. |
| 5,322,057 A | 6/1994 | Raabe et al. |

(Continued)

FOREIGN PATENT DOCUMENTS

WO        97/19719 A1    6/1997

OTHER PUBLICATIONS

PCT International Search Report and Written Opinion from corresponding PCT Application No. PCT/US2011/020155 on Apr. 7, 2011.

*Primary Examiner* — Rachel Young
(74) *Attorney, Agent, or Firm* — Andrus Intellectual Property Law, LLP

(57) ABSTRACT

A system and method for operating a ventilator to compensate for external gas flow reaching a patient from an external device, such as a nebulizer. A control unit of the ventilator monitors the gas flow rate from the ventilator and compares the gas flow rate from the ventilator to an expired gas flow rate from the patient. The difference between the inspired flow rate and the expired flow rate is due to the external device. The control unit modifies the operation of the ventilator to compensate for the external gas flow rate such that the flow of gas reaching the patient is maintained at a desired level.

12 Claims, 2 Drawing Sheets

(51) Int. Cl.
*A61M 16/14* (2006.01)
*A61M 16/20* (2006.01)

(56) References Cited

U.S. PATENT DOCUMENTS

| | | | |
|---|---|---|---|
| 5,666,946 | A | 9/1997 | Langenback |
| 7,267,121 | B2 | 9/2007 | Ivri |
| 7,331,339 | B2 | 2/2008 | Smith et al. |
| 7,549,421 | B2 | 6/2009 | Levi et al. |
| 2005/0284469 | A1 | 12/2005 | Tobia et al. |
| 2007/0157931 | A1 | 7/2007 | Parker et al. |
| 2008/0091117 | A1 | 4/2008 | Choncholas et al. |
| 2008/0142011 | A1 | 6/2008 | Aylsworth et al. |
| 2008/0295837 | A1 | 12/2008 | McCormick et al. |
| 2009/0293876 | A1 | 12/2009 | Soliman et al. |
| 2009/0320836 | A1 | 12/2009 | Baker, Jr. |
| 2010/0024819 | A1* | 2/2010 | Tiedje ............... 128/204.23 |
| 2010/0236555 | A1 | 9/2010 | Jafari et al. |
| 2011/0175728 | A1* | 7/2011 | Baker, Jr. ............... 340/540 |

* cited by examiner

COMPENSATION FOR UNMEASURABLE INSPIRATORY FLOW IN A CRITICAL CARE VENTILATOR

CROSSREFERENCE TO RELATED APPLICATIONS

This application is divisional of U.S. application Ser. No. 12/695,514, filed Jan 28, 2010, which application was published on Jul 28, 2011, as U.S. Publication Ser. No. 2011/0180063, the contents of which are incorporated herein by reference in Their entireties.

BACKGROUND OF THE INVENTION

The present disclosure generally relates to a method and system for providing ventilator therapy to a patient. More specifically, the present disclosure relates to a method of adjusting the operation of a ventilator to compensate for the flow of gas created by an external gas source, such as a nebulizer, to improve the ventilation therapy.

Clinicians commonly utilize a nebulizer to provide aerosoled drug delivery to a patient that is connected to a ventilator. Nebulizers are typically placed in the inspiratory limb of a patient circuit and are used to inject an aerosoled drug directly into the flow stream of the breathing gases for the patient. Nebulizers are typically pneumatic or ultrasonic technology-based devices that are run continuously for a period of time until delivery of discrete doses of the drug or agent have been completed.

Figure 1:
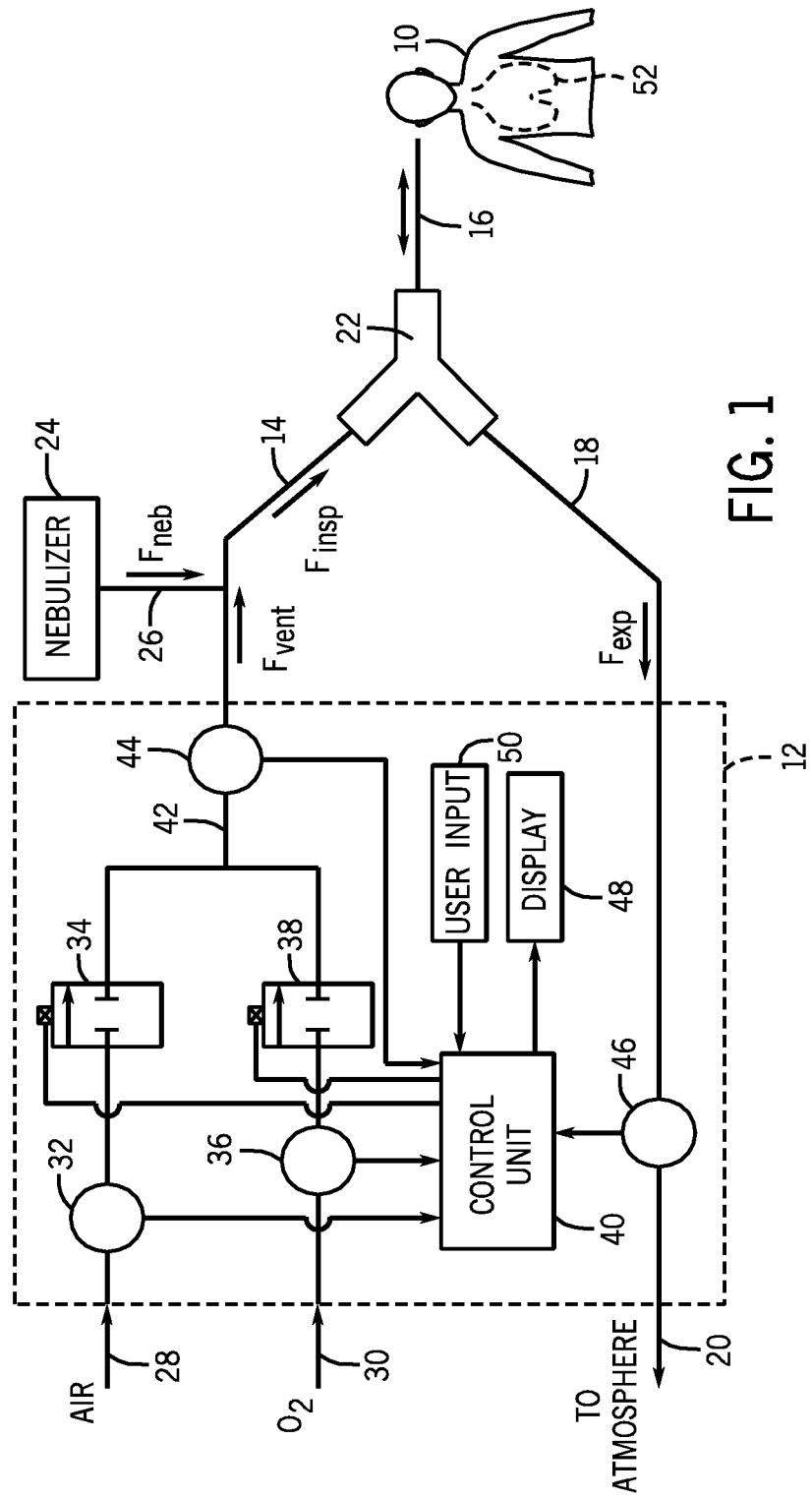
Figure 2:
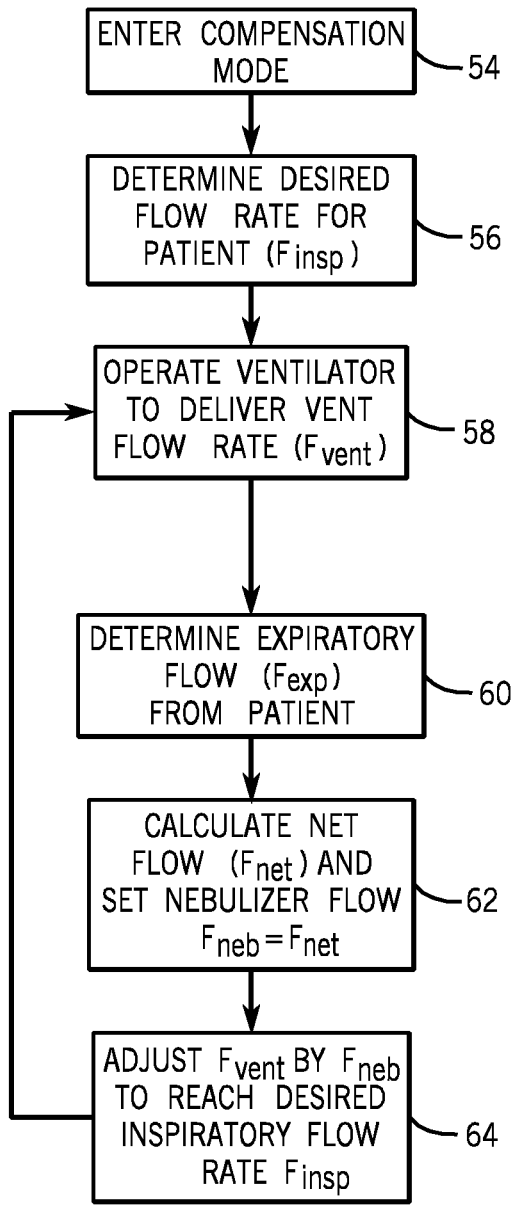

When utilizing a pneumatic nebulizer, the nebulized agent supplied to the patient is received from the nebulizer entrained in a nebulizer gas flow. The nebulizer gas flow including the entrained nebulized agent is added to the flow of gas from the ventilator such that the combined gas flow is provided to the patient during the inspiratory phase.

Although the use of a nebulizer to introduce a nebulized agent into the flow of gas to the patient functions well to deliver the nebulized agent, the addition of the nebulizer gas flow to the gas flow from the ventilator can create problems. In most modern ventilators, the flow of gas from the nebulizer is added downstream from the sensors that measure the inspiratory gas flow from the ventilator. In such an embodiment, the gas flow measured during the expiratory phase is higher than the corresponding inspiratory volume from the ventilator. The increased volume of the expiratory gas flow can lead to unnecessary alarm conditions in the ventilator. Without some type of compensation for the flow provided by the nebulizer or other external device, the ventilator can generate unnecessary alarms, which significantly reduces the reliability of the volumes measured during the inspiratory and expiratory phase. Alternatively, the patient could be overventilated due to the unmeasured inspiratory flow from the nebulizer.

SUMMARY OF THE INVENTION

The present disclosure relates to a method and system for operating a ventilator to compensate for external gas flows being provided to the patient downstream from the ventilator. The method and system allows the ventilator to compensate for the external gas flow rates without having to receive any information directly from the external device delivering the additional gas flow.

The ventilator includes a control unit that operates one or more valves to control the flow rate of one or more gases from the ventilator. An inspiratory flow sensor is included in the ventilator that allows the control unit to monitor the flow rate of gas leaving the ventilator. The ventilator further includes an expiratory flow sensor that receives and measures the flow of gas in the expiratory limb, which includes the flow from the patient during exhalation and any portion of the flow from the inspiratory limb that bypasses the patient. During normal operation without any external gas flow being provided to the patient other than from the ventilator, the net volume of gas measured over a breath cycle is approximately zero.

When an external device, such as a nebulizer, provides an external gas flow to the patient in addition to the gas flow from the ventilator, the difference between the flow rate determined by the inspiratory flow sensor and the flow rate determined by the expiratory flow sensor will not be zero due to the unmeasured external gas flow. The value of the net flow rate represents the gas flow from the external device, such as the nebulizer. Since the gas flow from the external device is injected into the gas flow downstream from the ventilator, the actual volume of gas inspired by the patient during each breath cycle is above a desired tidal volume set by the operator.

The control unit operates one or more flow valves contained within the ventilator to reduce the flow rate from the ventilator by the determined flow rate from the nebulizer. In this manner, the combined flow from the ventilator and the nebulizer will equal the desired inspiratory flow rate. By determining the external flow rate, the ventilator can reduce the flow from the ventilator and thus compensate for the external flow rate such that the actual flow rate of gas delivered to the patient is maintained at a desired level.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings:

FIG. 1 is a schematic illustration of a mechanical ventilator and nebulizer for ventilating a patient; and FIG. 2 is a flow chart illustrating the steps for adjusting the flow rate from the ventilator to compensate for the flow rate from a nebulizer.

DETAILED DESCRIPTION OF THE INVENTION

FIG. 1 illustrates a typical configuration of a ventilation system for providing a flow of ventilation gas to a patient 10. A ventilator 12 provides a flow of ventilation gas through an inspiratory limb 14 to the patient 10 through a patient conduit 16. Exhaled gases from the patient travel through the patient conduit 16 and through an expiratory limb 18 back to the ventilator 12. The expired gases from the patient are vented to atmosphere as indicated by the ventilation discharge 20. The inspiratory limb 14 and the expiratory limb 18 are connected to the patient conduit 16 through a wye piece 22. The patient can receive the flow of ventilation gas through various different interfaces such as a gas mask or a tracheal tube.

In the embodiment shown in FIG. 1, a nebulizer 24 is provided to medicate the patient on the ventilator. The nebulizer 24 introduces aerosolized medical agent into the flow of gas from the ventilator 12 in the inspiratory limb 14. The nebulized medical agent is entrained in a flow of gas in the nebulizer conduit 26. The nebulizer gas flow and nebulized agent combine with the flow of gas from the ventilator in the inspiratory limb 14 such that the combined gas flow is provided to the patient through the patient conduit 16.

Although a nebulizer 24 is shown in the embodiment of FIG. 1, it should be understood that other types of external devices could be utilized to introduce an external gas flow into the inspiratory limb 14 for ventilation therapy purposes. As an example, an external device that injects a vasal dilator could be utilized in place of the nebulizer 24. Such an external device provides an external flow of gas that is in addition to the gas flow from the ventilator 12.

The ventilator 12 shown in the embodiment of FIG. 1 is only one type of ventilator that could be utilized while operating within the scope of the present disclosure. Although the specific operating components of the ventilator 12 will be shown and described, it should be understood that various different types of ventilators, including different operating components, could be utilized while operating within the scope of the present disclosure.

In the embodiment shown in FIG. 1, the ventilator 12 receives air in conduit 28 from an appropriate source, not shown, such as a cylinder of pressurized air or a hospital air supply manifold. Ventilator 12 also receives pressurized oxygen in conduit 30, also from an appropriate source, not shown, such as a cylinder or manifold. The flow of air in ventilator 12 is measured by an air flow sensor 32 and controlled by an air flow valve 34. The flow of oxygen is measured by an oxygen sensor 36 and controlled by an oxygen valve 38. The operation of the valves 34, 38 is established by a control unit 40, such as a central processing unit (CPU) in the ventilator 12.

The air and oxygen are mixed in conduit 42 and pass through an inspiratory flow sensor 44 before exiting the ventilator 12 into the inspiratory limb 14. In the ventilator 12 shown in FIG. 1, the ventilator 12 includes both an air flow sensor 32 and an oxygen flow sensor 36 in addition to the inspiratory flow sensor 44. It should be understood that the air flow sensor 32 and the oxygen flow sensor 36 could be eliminated. The inspiratory flow sensor 44 provides an indication of the flow of the combined gas being delivered by the ventilator 12 to the inspiratory limb 14.

The expiratory limb 18 from the patient is also received at the ventilator 12 and the expired gas from the patient and any bypass flow from the inspiratory limb 14 passes through an expiratory flow sensor 46 before being discharged from the ventilator 12. The expiratory flow sensor 46 is in communication with the control unit 40 such that the control unit 40 can monitor the expiratory gas flow from the patient.

Ventilator 12 further includes a display 48 to provide visual indicators to medical personnel as to the current operating parameters for the ventilator 12. A user input device 50 allows the user to input operating parameters to the ventilator, as desired. One example of a ventilator 12 operating in accordance with the embodiment shown in FIG. 1 is the GE Healthcare Engstrom ventilator, although other types of ventilators are contemplated as being within the scope of the present disclosure.

During operation of the ventilator 12 when the nebulizer 24 is inactive, the ventilator 12 creates a gas flow rate from the ventilator $F_{vent}$ which is delivered to the patient through the inspiratory limb 14. When the nebulizer 24 is inactive, the inspired gas flow $F_{insp}$ delivered to the patient's lungs 52 through the patient conduit is equal to the ventilation gas flow rate $F_{vent}$ and is directly controlled by the ventilator 12. During exhalation by the patient 10, the gas flow $F_{exp}$ through the expiratory limb 18 passes through the expiratory flow sensor 46. During the operation of the ventilator 12, the sum of the flows measured by the inspiratory flow sensor 44 and the expiratory flow sensor 46 provides an indication at any given point in time the magnitude of the gas flow and in which direction the gas is flowing. Inspiratory flow (toward the patient) is considered positive and expiratory flow (away from the patient) is considered to be negative. Net flow from the patient can be represented as follows:

$$F_{net} = F_{insp} + F_{exp} \qquad \text{Equation 1}$$

If there is a constant flow of gas through the circuit and none of the gas is moving toward or away from the patient, the net flow value $F_{net}$ will be zero.

The control unit 40 can determine the volume of gas delivered toward the patient from the ventilator by accumulating all net flow $F_{net}$ that is in the positive direction over a breath period. The control unit 40 can determine the volume of gas returning from the patient $V_{exp}$ by accumulating all net flow $F_{net}$ that is in the negative direction over the same breath period. The control unit 40 can determine the volume of gas delivered toward the patient from the ventilator $V_{vent}$ by accumulating all net flow $F_{net}$ that is in the positive direction over the same breath period. The net volume $V_{net}$ is calculated utilizing the following equation:

$$V_{net} = V_{vent} + V_{exp} \qquad \text{Equation 2}$$

Without any external gas flow, the volume of gas in the expiratory limb, $V_{exp}$ should equal the volume of gas from the ventilator $V_{vent}$ so the net volume will be approximately zero.

As can be understood by the above description, the calculation of flow rate and volume are related to each other. The relationship between the flow rate and volume is important in understanding the description below.

In the embodiment shown in FIG. 1, when the nebulizer 24 is activated to deliver a nebulized agent to the patient, the nebulized agent is entrained in a flow of gas leaving the nebulizer 24 through the nebulizer conduit 26, as indicated by $F_{neb}$. Since the gas flow from the nebulizer enters the inspiratory limb 14 downstream from the inspiratory flow sensor 44, the nebulizer gas flow is unmeasured and the control unit 40 is unaware of the actual flow rate of gas reaching the patient. In the embodiment shown in FIG. 1, the actual flow of gas reaching the patient $F_{insp}$ is a combination of the gas flow from the ventilator $F_{vent}$ and the gas flow from the nebulizer $F_{neb}$, as can be represented by the following equation:

$$F_{insp} = F_{vent} + F_{neb} \qquad \text{Equation 3}$$

As can be understood by the above equation, if a user sets a desired gas flow to reach the patient in the ventilator 12, although the gas flow from the ventilator can be controlled by the control unit 40, the actual flow rate reaching the patient $F_{insp}$ will be elevated due to the flow of gas $F_{neb}$ from the nebulizer. It is desirable to thus operate the ventilator 12 to compensate for the external flow of gas from the nebulizer $F_{neb}$ such that the flow of gas to the patient $F_{insp}$ is maintained at the desired level.

The net flow of gas $F_{net}$ during a breath cycle can be written by the following equation, which takes into account the nebulizer gas flow $F_{neb}$:

$$F_{net} = (F_{vent} + F_{neb}) + F_{exp} \qquad \text{Equation 4}$$

As can be understood by the above equation, the flow rate of gas from the nebulizer $F_{neb}$ can be determined by the control unit based upon the measurements taken by the inspiratory flow sensor 44 and the expiratory flow sensor 46 taken over the same sample time period.

Once the flow from the nebulizer $F_{neb}$ has been determined, control unit 40 can then utilize Equation 3 to reduce the flow from the ventilator $F_{vent}$ such that the inspired gas flow $F_{insp}$ reaches the desired value based on an input from the user in the ventilator 12. Typically, a user will specify a desired tidal volume for the patient by entering the desired tidal volume through the user input 50 which is in communication with the control unit 40. The tidal volume is a volume of gas to be delivered to the patient during each breath cycle. Based upon this desired tidal volume and other breath settings entered by the user, the control unit 40 can calculate a flow rate $F_{insp}$ required to obtain that volume over the inspiratory period of the breath cycle. Based upon the desired inspiratory gas flow $F_{insp}$, the control unit 40 compensates for the external gas flow from the nebulizer $F_{neb}$ and reduces the flow of gas from the ventilator $F_{vent}$ by an amount corresponding to the determined nebulizer gas flow.

Gas flow rates are represented as volume per unit time (e.g. mL/min and L/sec) so the net volume over some sample periods can be used to determine the external flow rate of the nebulizer. Net volume is expected to be at its minimum at the end of each complete breath period and therefore external flow estimates are typically updated at the end of each breath period. In the embodiment shown, the ventilator 12 will average the estimated external flow rates over a series of consecutive breaths. Typically, enough breaths are included in the average such that the sample period is at least 20 seconds to smooth out any breath-to-breath fluctuation in the external flow estimates.

By utilizing the method and system described above, the output of the ventilator $F_{vent}$ can be reduced to meet the inspiratory volume requirements $F_{insp}$ by including the flow of gas from the nebulizer $F_{neb}$. The volume of gas being delivered to the patient will be a more accurate representation of the desired volume to be delivered and alarms included in the ventilator 12 will be less sensitive and the displayed values on the display 48 will become more accurate.

The use of the inspiratory flow sensor 44 and the expiratory flow sensor 46 contained within the ventilator 12 is more desirable than positioning a flow sensor in the inspiratory limb 14 downstream from the nebulizer 24. The gas flow leaving the nebulizer includes a nebulized medical agent, which can coat hotwire flow sensors and lead to inaccurate and unreliable measurements. Since the flow sensors 44 and 46 are contained within the ventilator, no additional components are needed to operate the ventilator in the compensation mode previously described.

FIG. 2 illustrates one method of operating the control unit to compensate for the external gas flow from the nebulizer. As shown, the control unit 40 first determines in step 54 whether the control unit 40 should operate within the compensation mode. The user can select the compensation mode through an input at the user input 50.

If the control unit 40 determines in step 54 that the ventilator should be operated in the compensation mode, the control unit first determines the desired flow rate for the patient ($F_{insp}$) in step 56. As set forth previously, the user typically enters a desired tidal volume for each breath through the user input device 50. Typically, the desired tidal volume for the patient is selected based upon the size of the patient, the condition of the patient and other parameters that are typically used to determine ventilation rates, as is well known to those of ordinary skill in the art. Based on the desired tidal volume, the control unit 40 calculates the desired flow rate needed to deliver the tidal volume.

Once the desired flow rate for the patient has been determined, the control unit 40 operates the ventilator 12 to deliver the ventilation flow rate ($F_{vent}$) where the ventilation flow rate is initially equal to the desired flow rate ($F_{insp}$). When operating the ventilator according to one contemplated embodiment, the control unit 40 initially assumes that no additional flow is being added to the flow from the ventilator ($F_{vent}$) such that the flow from the ventilator ($F_{vent}$) is assumed to be equal to the inspiratory flow ($F_{insp}$) to the patient.

Although the above method of operating the ventilator may be used, if an external flow of gas is present, such as the nebulizer flow rate $F_{neb}$, the patient would receive the nebulizer gas flow on top of the ventilator gas flow for at least the first breath, which could lead to over-ventilation of the patient until the nebulizer gas flow is calculated. In an alternate embodiment, the control unit assigns a reference value for the nebulizer gas flow at the start of operation and the ventilator gas flow ($F_{vent}$) is reduced by the reference gas flow rate assigned to the nebulizer. In this manner, the initial gas flow rate supplied to the patient may be less than the desired flow rate ($F_{insp}$) when no external gas flow rate is present. However, under-ventilation of the patient has been found to be more desirable than an over-ventilation. It is contemplated that the operator of the ventilator can enter the reference flow rate into the control unit based on the expected flow rate from the external gas source, such as the nebulizer. The control unit will use the expected flow rate from the ventilator as the reference flow rate until an actual estimation of the nebulizer flow rate is made.

Once the ventilator begins to deliver the ventilation gas to the patient, the control unit 40 then monitors the expiratory flow rate ($F_{exp}$) from the patient through the expiratory flow sensor 46, as indicated in step 60. As previously described, if the nebulizer 24 is not operating, the net volume ($V_{net}$), as indicated by Equation 2 above, will be approximately zero.

However, if the nebulizer 24 is operating to deliver a nebulized medical agent, the calculated net volume ($V_{net}$) of gas will not be zero. As described, the net volume represents the volume of gas from the nebulizer ($V_{neb}$). The net volume of gas is determined over a sample period, such as a single breath or a series of breaths, and is normalized to a minute such that the control unit 40 can calculate the flow rates that are used throughout the control of the ventilator. Typically, the flow rates are determined as mL/min. In step 62, the control unit sets the nebulizer flow rate ($F_{neb}$) to be equal to the net flow rate ($F_{net}$).

Once the control unit 40 determines the nebulizer flow rate ($F_{neb}$), the control unit reduces the target flow rate ($F_{insp}$) by the flow rate of the gas from the nebulizer ($F_{neb}$), which is used as the updated ventilator flow rate ($F_{vent}$). In this manner, the desired flow rate to the patient ($F_{insp}$) returns to its desired value, as indicated by step 64. As described, the control unit compensates for the external flow from the nebulizer 24 to adjust the flow rate from the ventilator such that the desired inspiratory flow rate reaching the patient remains at the desired value. Without the use of the external flow compensation, the inspiratory flow rate to the patient is elevated by the flow rate of gas from the nebulizer, which results in the patient receiving a greater than desired gas flow.

In one contemplated embodiment, the control unit limits the value of the estimated nebulizer flow rate ($F_{neb}$) based on the estimate entered into the ventilator. The limit on the value of the nebulizer flow rate prevents the control unit from reducing the ventilator gas flow ($F_{vent}$) too far, which could result in inadequate flow to the patient for ventilation. Since the estimated nebulizer flow rate is based on the inspiratory and expiratory sensors, which may suffer from sensor drift, limiting the estimated value for the nebulizer flow rate insures that at least a minimum gas flow rate is delivered by the ventilator. The minimum flow rate depends on the desired flow rate, which is based on the desire tidal volume entered by the user.

Although step 64 contemplates a reduction in the flow of gas from the ventilator ($F_{vent}$) by the flow of the gas from the nebulizer ($F_{neb}$), it should be understood that the control unit could need to increase the flow of gas from the ventilator ($F_{vent}$) during the operation of the ventilator, such as when the nebulizer is turned off or when the flow of gas from the nebulizer decreases. Thus, the control unit adjusts the flow of gas from the ventilator ($F_{vent}$) such that the combination of the ventilator gas flow and the nebulizer gas flow reaches the desired flow rate to the patient ($F_{insp}$).

Once the control unit adjusts the ventilator flow rate in step 64, the control unit returns to step 58 and operates the ventilator to deliver the adjusted ventilation flow rate ($F_{vent}$). The control unit continues to operate steps 58-64 to deliver the desired flow rate of gas to the patient in the manner described.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of operating a ventilator to provide an inspiratory gas flow to a patient including an external gas flow from a medical device that operates separately and independently from the operation of the ventilator and without communication with the ventilator, the method comprising the steps of:
    setting a desired inspiratory flow rate in a control unit of the ventilator;
    monitoring a flow of gas from only the ventilator in the control unit of the ventilator utilizing an inspiratory sensor of the ventilator;
    monitoring an expiratory flow of gas from the patient in the control unit of the ventilator utilizing an expiratory sensor of the ventilator;
    determining an external flow rate from the medical device in the control unit of the ventilator based on the difference between the expiratory flow rate and the ventilator flow rate; and
    operating the control unit of the ventilator to reduce the ventilator flow rate based upon the determined external flow rate such that the combination of the reduced ventilator flow rate and the external flow rate provides the desired inspiratory flow rate to the patient.

2. The method of claim 1 wherein the flow of gas from the ventilator and the expiratory flow of gas are determined by the inspiratory sensor and the expiratory sensor contained within the ventilator.

3. The method of claim 2 wherein the external gas flow is injected into the flow of gas from the ventilator downstream from the inspiratory sensor contained within the ventilator.

4. The method of claim 1 wherein the external gas is provided by a nebulizer that provides a nebulized agent in a nebulizer gas flow.

5. The method of claim 1 wherein the desired inspiratory flow rate for the patient is determined in the control unit of the ventilator based upon user input.

6. The method of claim 5 wherein the desired inspiratory flow rate is determined through the user input entered into a user input device of the ventilator, wherein the user input device is coupled to the control unit.

7. A method of adjusting a flow rate from a ventilator to compensate for a gas flow from a nebulizer that operates separately and independently from the operation of the ventilator and without communication with the ventilator to provide a desired inspiratory flow rate to a patient, comprising the steps of:
    setting a desired inspiratory flow rate in a control unit of the ventilator;
    monitoring the flow of gas from only the ventilator in the control unit of the ventilator utilizing an inspiratory sensor of the ventilator;
    monitoring an expiratory flow of gas from the patient utilizing an expiratory sensor of the ventilator;
    determining a nebulizer flow rate in the control unit of the ventilator based upon the difference between the expiratory flow rate and the ventilator flow rate; and
    operating the control unit of the ventilator to reduce the ventilator flow rate such that the combination of the nebulizer flow rate and the ventilator flow rate reaches the desired inspiratory flow rate.

8. The method of claim 7 wherein the flow of gas from the ventilator and the expiratory flow are determined by the inspiratory sensor and the expiratory sensor contained within the ventilator.

9. The method of claim 8 wherein the nebulized agent is injected into the flow of gas from the ventilator downstream from the inspiratory sensor contained within the ventilator.

10. The method of claim 7 wherein the desired inspiratory flow rate for the patient is determined in the control unit of the ventilator based upon user input.

11. The method of claim 10 wherein the desired inspiratory flow rate is determined based on a desired breath volume entered into a user input device of the ventilator, wherein the user input device is coupled to the control unit.

12. The method of claim 7 further comprising the steps of:
    assigning a reference flow rate to the nebulizer flow rate prior to determination of the nebulizer flow rate;
    reducing the flow rate from the ventilator by the reference flow rate; and
    providing the reduced ventilator flow rate to the patient prior to determining the nebulizer flow rate.

* * * * *